United States Patent [19]
Yoon

[11] Patent Number: 5,972,001
[45] Date of Patent: Oct. 26, 1999

[54] METHOD OF LIGATING ANATOMICAL TISSUE WITH A SUTURE SPRING DEVICE

[76] Inventor: InBae Yoon, 2101 Highland Ridge Dr., Phoenix, Md. 21131

[21] Appl. No.: 09/012,410

[22] Filed: Jan. 23, 1998

Related U.S. Application Data

[63] Continuation of application No. 08/758,160, Nov. 25, 1996.

[51] Int. Cl.⁶ ..................................................... A61B 17/10
[52] U.S. Cl. .......................... 606/139; 604/144; 604/148
[58] Field of Search ..................................... 606/139, 140, 606/141, 144, 157, 158, 148

[56] References Cited

U.S. PATENT DOCUMENTS

| | | |
|---|---|---|
| 816,026 | 3/1906 | Meier . |
| 1,123,290 | 1/1915 | Von Herff . |
| 2,817,339 | 12/1957 | Sullivan . |
| 3,091,828 | 6/1963 | Soltis . |
| 3,446,212 | 5/1969 | Le Roy . |
| 3,545,444 | 12/1970 | Green . |
| 3,604,425 | 9/1971 | Le Roy . |
| 3,716,058 | 2/1973 | Tanner, Jr. . |
| 3,735,762 | 5/1973 | Bryan et al. . |
| 3,870,048 | 3/1975 | Yoon . |
| 3,939,828 | 2/1976 | Mohr et al. . |
| 3,989,049 | 11/1976 | Yoon . |
| 4,217,902 | 8/1980 | March . |
| 4,316,469 | 2/1982 | Kapitanov . |
| 4,337,774 | 7/1982 | Perlin . |
| 4,484,581 | 11/1984 | Martin et al. . |
| 4,485,816 | 12/1984 | Krumme . |
| 4,535,772 | 8/1985 | Sheehan . |
| 4,548,201 | 10/1985 | Yoon . |
| 4,595,007 | 6/1986 | Mericle . |
| 4,637,395 | 1/1987 | Caspar et al. . |
| 4,777,950 | 10/1988 | Kees, Jr. . |
| 4,791,707 | 12/1988 | Tucker . |
| 4,794,927 | 1/1989 | Yoon . |
| 4,869,268 | 9/1989 | Yoon . |
| 4,924,866 | 5/1990 | Yoon . |
| 4,950,258 | 8/1990 | Kawai et al. . |

(List continued on next page.)

FOREIGN PATENT DOCUMENTS

| | | |
|---|---|---|
| 9505778 | 3/1995 | WIPO . |
| WO96/03925 | 2/1996 | WIPO . |

*Primary Examiner*—Michael Buiz
*Assistant Examiner*—Julian W. Woo
*Attorney, Agent, or Firm*—Blank Rome Comisky & McCauley LLP

[57] ABSTRACT

A method of ligating anatomical tissue using a suture spring device of coiled configuration includes expanding the suture spring device from a relaxed, unexpanded state to an elastically deformed, expanded state, positioning the anatomical tissue in an axial space between rings or coils of the suture spring device when the device is in the elastically deformed, expanded state, and allowing the suture spring device to contract from the expanded state toward the unexpanded state to ligate the anatomical tissue. The rings or coils of the suture spring device can be axially and/or radially expanded in the elastically deformed, expanded state. In the case of the rings being radially expanded, the anatomical tissue is preferably repositioned to be disposed concentrically within a central longitudinal passage or aperture of the suture spring device so that the rings are coiled around the anatomical tissue in the expanded state and able to apply a radially compressive force when contracted. In the case of the rings being axially expanded, the anatomical tissue is maintained in the axial space between rings when the suture spring device is in the expanded state so that, when the device is allowed to contract, an axially compressive force is applied which will ligate the anatomical tissue.

25 Claims, 2 Drawing Sheets

U.S. PATENT DOCUMENTS

| | | |
|---|---|---|
| 4,961,743 | 10/1990 | Kees, Jr. et al. . |
| 4,979,954 | 12/1990 | Gwathmey et al. . |
| 4,990,152 | 2/1991 | Yoon . |
| 5,007,921 | 4/1991 | Brown . |
| 5,026,379 | 6/1991 | Yoon . |
| 5,026,390 | 6/1991 | Brown . |
| 5,030,224 | 7/1991 | Wright et al. . |
| 5,035,692 | 7/1991 | Lyon et al. . |
| 5,047,047 | 9/1991 | Yoon . |
| 5,053,047 | 10/1991 | Yoon . |
| 5,158,566 | 10/1992 | Pianetti . |
| 5,171,252 | 12/1992 | Friedland . |
| 5,174,276 | 12/1992 | Crockard . |
| 5,207,692 | 5/1993 | Kraus et al. . |
| 5,217,473 | 6/1993 | Yoon . |
| 5,222,976 | 6/1993 | Yoon . |
| 5,226,908 | 7/1993 | Yoon . |
| 5,242,456 | 9/1993 | Nash et al. . |
| 5,309,927 | 5/1994 | Welch . |
| 5,330,503 | 7/1994 | Yoon . |
| 5,334,209 | 8/1994 | Yoon . |
| 5,342,373 | 8/1994 | Stefanchik et al. . |
| 5,356,424 | 10/1994 | Buzerak et al. . |
| 5,439,457 | 8/1995 | Yoon . |
| 5,476,505 | 12/1995 | Limon . |
| 5,486,187 | 1/1996 | Schenck . |
| 5,499,990 | 3/1996 | Schülken et al. . |
| 5,522,822 | 6/1996 | Phelps et al. . |
| 5,562,685 | 10/1996 | Mollenauer et al. . |
| 5,582,616 | 12/1996 | Bolduc et al. . |

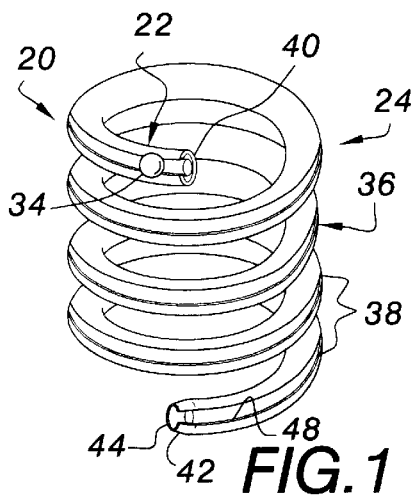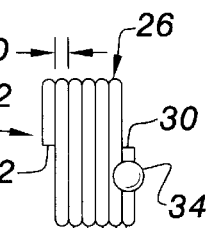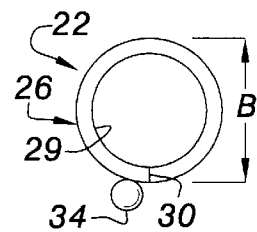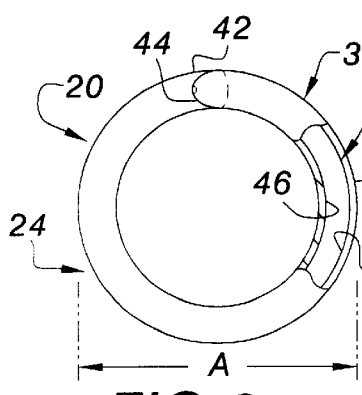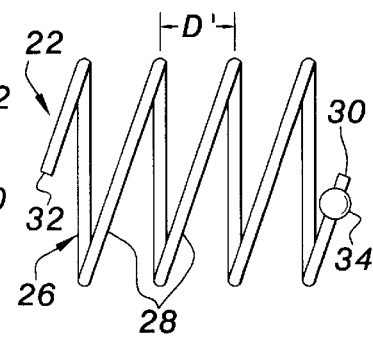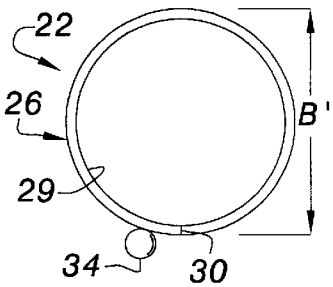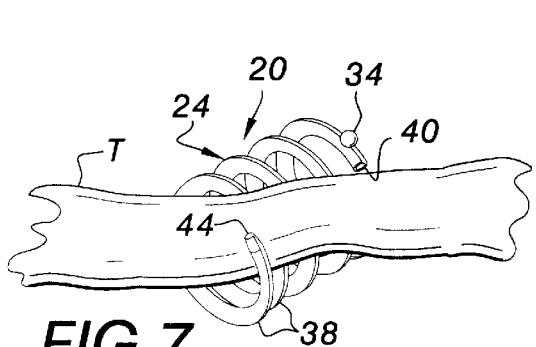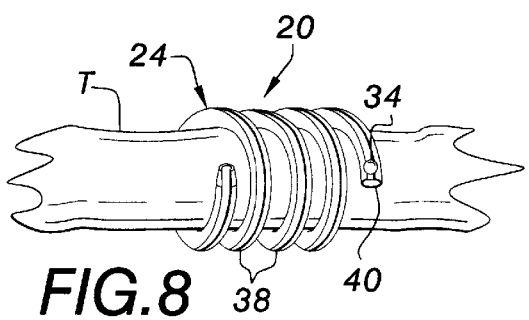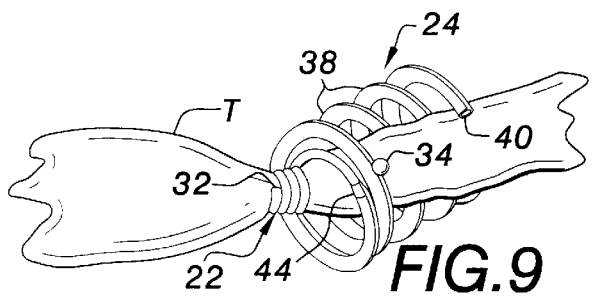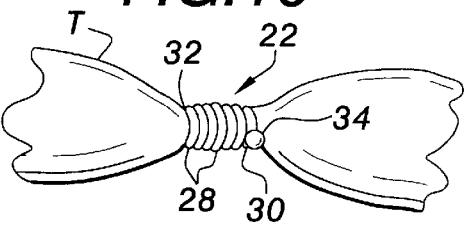

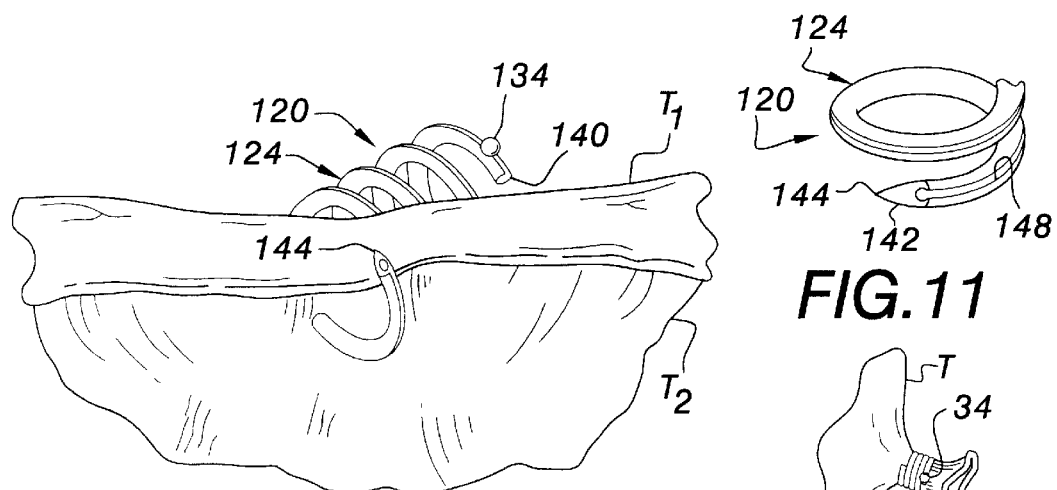
FIG. 11
FIG. 12
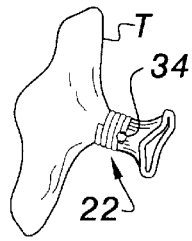
FIG. 19
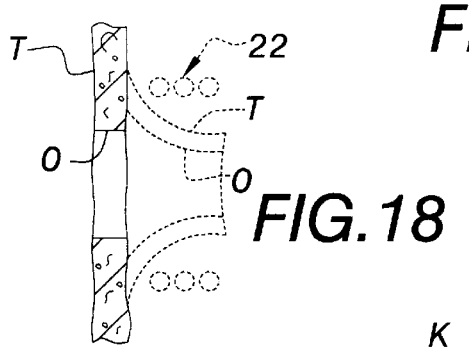
FIG. 18
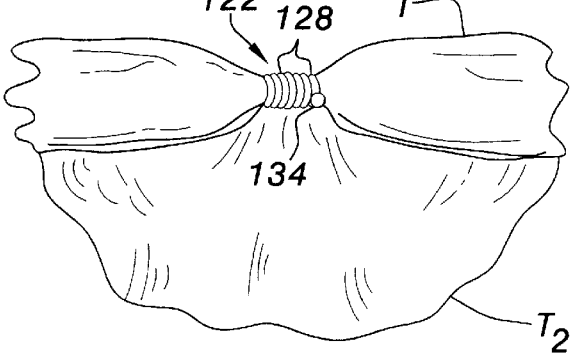
FIG. 13
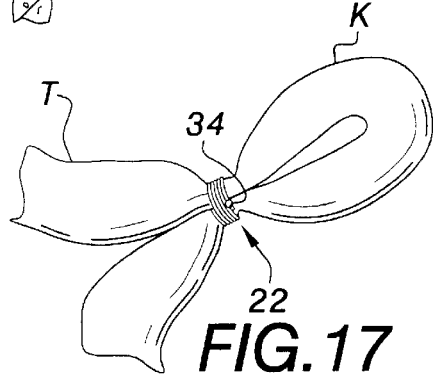
FIG. 17
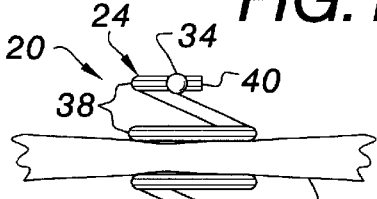
FIG. 15
FIG. 14
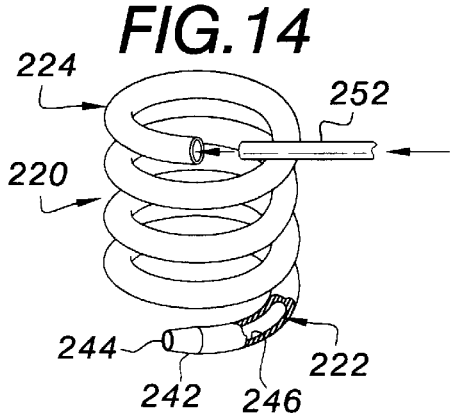
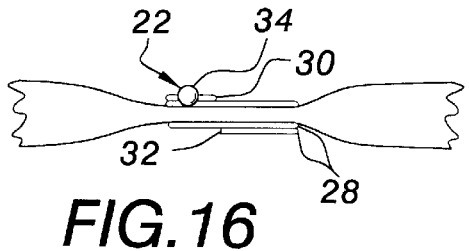
FIG. 16

METHOD OF LIGATING ANATOMICAL TISSUE WITH A SUTURE SPRING DEVICE

This application is a continuation of patent application Ser. No. 08/758,160, filed on Nov. 25, 1996.

BACKGROUND OF THE INVENTION

1. Field of the Invention

The present invention relates to methods of ligating anatomical tissue and, more particularly, to a method of ligating anatomical tissue using suture spring devices such as those described in my patent application Ser. No. 08/610,951, filed Mar. 5, 1996 and entitled "Suture Spring Device," the disclosure of which is incorporated herein by reference.

2. Discussion of the Prior Art

Closed or endoscopic operative procedures, also known as least-invasive procedures, have become extremely popular for use in many areas such as laparoscopy (pelviscopy), gastroentroscopy, laryngobronchoscopy and arthroscopy. In endoscopic operative procedures, access to an internal operative site in the body is gained through a relatively narrow or small size endoscopic portal establishing communication with the internal operative site from externally of the body. Accordingly, various instruments can be introduced at the operative site via the portal without the need for a skin incision of substantial size as is typically required for open procedures. Endoscopic procedures provide many benefits over open procedures including minimal invasiveness and trauma, fewer complications, shorter wound healing times, less patient discomfort, shorter hospitalization and rehabilitation times, cost savings and the ability to perform surgery without general anesthesia and in non-hospital or out-patient sites.

Ligating or tying anatomical tissue is a time consuming and tedious part of both endoscopic and non-endoscopic operative procedures due to the difficulty involved in tying or applying an occluding ligature to the anatomical tissue as is desirable and/or necessary in many various procedures. Ligating anatomical tissue is particularly difficult in endoscopic procedures due to the constraints on access to the operative site, the limited room for maneuverability at the operative site and the procedural or operational complexity required of many conventional endoscopic ligating instruments. Accordingly, the advantages of endoscopic procedures are sometimes outweighed by the disadvantages caused by the increased difficulty to ligate or tie and the increased length of time required to perform endoscopic procedures where such time is significantly extended due to the time required for ligation or tying.

Because endoscopic procedures are preferred over open procedures, much effort has been spent to develop instruments and techniques for facilitating anatomical tissue ligation. One technique, as exemplified by U.S. Pat. No. 3,545,444 to Green, involves the use of a wire suture which is bent into a coiled shape about an occluded tubular member to hold the tubular member in the occluded state. The wire suture is formed of a ductile material which, when bent, will tend to remain in the bent condition and not contract further to compensate for shrinkage or other changes in the condition of the tubular member. Various other ligating devices or instruments have been proposed, as exemplified by U.S. Pat. No. 3,735,762 to Bryan et al, U.S. Pat. No. 4,337,774 to Perlin, U.S. Pat. No. 4,484,581 to Martin, U.S. Pat. No. 4,777,950 to Keys, Jr., U.S. Pat. No. 5,171,252 to Friedland, and U.S. Pat. No. 5,342,373 to Stefanchik; however, no alternative technique has yet been well accepted by surgeons to produce the results obtained by conventional methods of ligating. Thus, there remains a great need for ligating techniques useful in endoscopic and open surgery that permit surgeons to ligate anatomical tissue in a time efficient, consistent and precise manner.

SUMMARY OF THE INVENTION

Accordingly, it is a primary object of the present invention to overcome the above-mentioned disadvantages of the prior art and to provide an improved method of ligating anatomical tissue.

Another object of the present invention is to use contraction of a suture spring device to ligate anatomical tissue in a time efficient, consistent and precise manner.

A further object of the present invention is to form a ligature around anatomical tissue by threading a suture spring device of coiled configuration around the tissue in an elastically deformed, radially expanded state and allowing the suture spring device to contract radially to ligate the anatomical tissue.

Still another object of the present invention is to ligate anatomical tissue with a suture spring device of coiled configuration by positioning the tissue in an axial space between rings of the suture spring device when the device is in an elastically deformed, axially expanded state and by then allowing the suture spring device to contract axially to ligate the anatomical tissue.

The present invention has another object in using a guide to position a coiled suture spring device around anatomical tissue in an elastically deformed, expanded state so that, when the guide is removed, the suture spring device will contract to ligate the anatomical tissue.

Some of the advantages of the present invention over the prior art are that ligating anatomical tissue is facilitated in both endoscopic and non-endoscopic procedures, that the ligating method can be easily adapted for anatomical tissue of various size, shape and position within the body, that anatomical tissue can be ligated over relatively large areas or at spaced locations depending upon the type of suture spring device used, that a plurality of ligating suture spring devices can be disposed within a guide and/or carried by a suture spring device applicator to permit anatomical tissue to be ligated at multiple locations within the body without the need of having to withdraw the guide or applicator from the body for reloading, and that the ligating method is more reliable than methods employing clips or clamps which can come loose or slip and is more efficient than methods involving lengths of filamentary suture material which must be knotted.

These and other objects, advantages and benefits are realized with the present invention as generally characterized in a method of ligating anatomical tissue using a suture spring device of coiled configuration including the steps of expanding the suture spring device from a relaxed, unexpanded state to an elastically deformed, expanded state, positioning the anatomical tissue in an axial space between rings of the suture spring device when the device is in the elastically deformed, expanded state, and causing the suture spring device to contract from the elastically deformed, expanded state toward the relaxed, unexpanded state to ligate the anatomical tissue. When rings of the suture spring device are radially expanded, the anatomical tissue can be positioned in the axial space between a distal tip of the suture spring device and a ring axially spaced from the tip. The suture spring device is then rotated to cause the tip of the device and the rings to travel or coil around the anatomical tissue so that, when the suture spring device is allowed to contract, the rings of the device will surround the anatomical tissue and exert a radially compressive force to ligate the tissue disposed therein. When the suture spring device is expanded by increasing the axial spacing between rings, the anatomical tissue can be placed in the axial space between the rings so that, when the suture spring is allowed to contract, the rings will exert an axially compressive force to ligate the anatomical tissue disposed therebetween.

Another aspect of the present invention is generally characterized in a suture spring device and a guide for positioning the suture spring device in relation to anatomical tissue in an elastically deformed, expanded state. The suture spring device includes an elastic body of coiled configuration having a relaxed, contracted state and an elastically deformed, expanded state. The guide includes an elongate tubular body of coiled configuration having a blunt distal tip and a configuration to hold the suture spring device in the elastically deformed, expanded state. The guide is removable from the suture spring device to permit the suture spring device to move resiliently from the expanded state toward the contracted state to ligate anatomical tissue engaged by the coiled body of the device.

A further aspect of the present invention is generally characterized in a method of ligating anatomical tissue using a suture device of coiled configuration including a plurality of connected rings including the steps of holding the suture device in an expanded state, positioning the anatomical tissue in an axial space between rings of the suture device when the device is in the expanded state, and causing the suture device to move from the expanded state toward the contracted state to ligate the anatomical tissue. When the anatomical tissue is positioned in the axial space between a distal tip of the suture device and a ring axially spaced from the tip, the device can be rotated to cause the tip of the device and the rings to coil around the anatomical tissue so that, if the suture spring device is caused to contract radially inward, the rings of the device will exert a radially compressive force to ligate the tissue disposed therein. When the suture device is caused to contract axially, the anatomical tissue can be placed in the axial space between rings so that, when the suture spring contracts axially, the rings will exert an axially compressive force to ligate the anatomical tissue disposed therebetween.

Other objects and advantages of the present invention will become apparent from the following description of the preferred embodiments taken in conjunction with the accompanying drawings, wherein like parts in each of the several figures are identified by the same reference numerals or by reference numerals having the same last two digits.

BRIEF DESCRIPTION OF THE DRAWINGS

FIG. 1 is a perspective view of a suture spring device and guide for ligating anatomical tissue according to the present invention.

FIG. 2 is a bottom view, partly in section, of the suture spring device and guide shown in FIG. 1.

FIGS. 3 and 4 are side and rear elevational views, respectively, of the suture spring device of FIG. 1 in a relaxed, contracted state.

FIGS. 5 and 6 are side and rear elevational views, respectively, of the suture spring device of FIG. 1 in an elastically deformed, expanded state.

FIGS. 7–10 are fragmentary perspective views illustrating a method of ligating anatomical tissue using a suture spring device according to the present invention.

FIG. 11 is an enlarged, fragmentary perspective view illustrating a modification of the guide according to the present invention.

FIGS. 12 and 13 are fragmentary perspective views illustrating use of the modified guide of FIG. 11 to ligate anatomical tissue according to the present invention.

FIG. 14 is a perspective view, partly in section, of a modified suture spring device and guide according to the present invention.

FIGS. 15 and 16 are fragmentary side views illustrating another method of ligating anatomical tissue using a suture spring device according to the present invention.

FIG. 17 is a fragmentary perspective view illustrating still another method of ligating anatomical tissue using a suture spring device according the present invention.

FIGS. 18 and 19 are a fragmentary sectional side view and a perspective view, respectively, illustrating use of a suture spring device to close an opening in anatomical tissue according to the present invention.

DESCRIPTION OF THE PREFERRED EMBODIMENTS

The suture spring device and method according to the present invention are described herein for use in ligating tubular anatomical tissue structures. It will be appreciated, however, that the suture spring device and method can be used to ligate any type of anatomical tissue including, but not limited to, tubular anatomical structures and anatomical tissue containing tubular anatomical structures.

A system 20 for ligating anatomical tissue according to the present invention, as illustrated in FIGS. 1 and 2, includes a suture spring device 22 and a guide 24 for positioning the device in relation to anatomical tissue in an elastically deformed, expanded state. Suture spring device 22 is of coiled configuration and, as best seen in FIGS. 3 and 4, the device includes an elongate, wire-like spring body 26 defining a series of connected coils or rings 28 of generally circular configuration, the rings being of like diameter and extending between proximal and distal ends 30 and 32 of the spring body concentric with a longitudinal axis of the device. A knob or handle 34 in the form of a ball is carried on an outer peripheral, convex edge or surface of the spring body near proximal end 30 and extends radially or laterally outward relative to the longitudinal axis of the suture spring device. Body 26 of the suture spring device is circular in transverse cross-section with a diameter or gage to permit the suture spring device to be deformed from the relaxed, contracted state shown in FIGS. 3 and 4, where rings 28 are collapsed against one another in abutting relation, to the expanded state shown in FIGS. 5 and 6, where the rings are held in an elastically deformed, radially expanded state to define a central, tissue receiving aperture or passage 29 of generally circular cross-section concentric with the longitudinal axis of the device. The spring body is formed of an elastic or resilient material, that is, a material able to recover its original shape or position after having been deformed, so that, when the expanded suture spring device is removed from the guide, the device will relax or tend to move resiliently from the expanded state toward the fully contracted state to engage and ligate any anatomical tissue disposed in the central passage defined by the rings. Any medically acceptable bioabsorbable or non-bioabsorbable elastic material can be used for the suture spring device including, but not limited to, titanium, nickel-titanium alloys, stainless steel and plastics such as nylon.

Guide 24 includes a hollow, tubular body 36 of coiled configuration defining a series of connected coils or rings 38 of generally circular configuration between a proximal end 40 and a distal end 42, the distal end terminating in a blunt, rounded tip 44. Referring to FIGS. 1–4, it can be seen that rings 38 of the guide body have a predetermined radius of curvature or diameter A greater than the diameter B of rings 28 of the suture spring device in the relaxed, contracted state. The rings of the guide also have a predetermined longitudinal or axial spacing C therebetween greater than the axial spacing D between rings 28 of the suture spring device in the relaxed, contracted state so that the suture spring device will be axially and radially expanded when it is disposed within the guide. The rings of the guide are hollow to define a lumen 46 through the body of the guide with a slot 48 along an outer peripheral, convex edge of the body communicating between an outer surface 50 of the guide and the lumen. The lumen is of sufficient size to receive and hold the body of suture spring device 22 while slot 48 is preferably V-shaped in transverse cross-section and somewhat narrower in width than the diameter of the spring body to allow knob 34 of the suture spring device to protrude from and slide within the slot while preventing the body of the spring from slipping therethrough. The guide can be made of any suitable medically acceptable material, such as stainless steel, so long as it is configured to have a stiffness suitable for maintaining the suture spring device in an expanded state while being positioned in relation to anatomical tissue to be ligated.

Suture spring device 22 is normally supplied separate from guide 24 in the relaxed, fully contracted state shown in FIGS. 3 and 4 with rings 28 collapsed against one another in abutting relation. Suture spring device 22 is preferably loaded into the guide and placed around anatomical tissue using a suture spring device applicator, such as the applicator described in my co-pending patent application Ser. No. 08/610,735, filed Mar. 5, 1996 and entitled "Suture Spring Device Applicator," the disclosure of which is incorporated herein by reference; however, the suture spring device and guide can be assembled together manually, for example by grasping the suture spring device and the guide, inserting distal end 32 of the suture spring device in open proximal end 40 of the guide and screwing the device lengthwise into the lumen of the guide. The spring is radially and axially expanded as it is screwed into the lumen, that is, the radius of curvature of rings 28 is gradually increased while the rings are separated from one another and maintained in the radially expanded and axially spaced condition within the guide as shown in FIGS. 1 and 2 so that the axial spacing D' between rings 28 of the suture spring device and the diameter B' of the rings in the elastically deformed, expanded state is about the same as the axial spacing C and diameter A of the guide rings. Knob 34 at the proximal end of the spring is aligned with slot 48 in the guide so that, as the suture spring device is loaded into the guide, the inner portion of the knob immediately adjacent the body of the suture spring device will enter into and slide along the slot while the outer portion of the knob will protrude outwardly of the slot in a radial or lateral direction relative to the longitudinal axis of the guide. In the fully assembled condition, shown in FIGS. 1 and 2, proximal end 30 of the suture spring device is disposed adjacent proximal end 40 of the guide and distal end 32 of the suture spring device is proximally spaced from the blunt tip 44 at the distal end of the guide. It will be appreciated, however, that the suture spring device can occupy less than the total number of rings of the guide in the elastically deformed, expanded state depending upon the length of the guide and the desired occluding length for the anatomical tissue. Also, more than one suture spring device can be disposed within a single guide if desired.

The suture spring device according to the present invention can be used in a number of ways to ligate anatomical tissue where by "ligate" is meant to tie-off or bind by application of a compressive force in order to change a condition of the anatomical tissue. A first method of ligating anatomical tissue using suture spring device 22 is illustrated in FIGS. 7–10 where the anatomical tissue T is shown as a tubular anatomical structure. Referring to FIG. 7, guide 24 is positioned alongside the structure T and moved to slip the structure into the axial space between the blunt tip 44 of the guide and the ring 38 immediately proximally adjacent the tip. With structure T positioned in the axial space between the tip and the adjacent ring as shown in FIG. 7, guide 24 is rotated in a clockwise direction, looking distally along the longitudinal axis of the guide, to reposition the structure relative to the guide as shown in FIG. 8. As the guide is rotated, tip 44 travels around the tubular structure in a distal direction establishing a helical path around the structure which is followed by the rest of the rings until the guide is coiled around the structure in a concentric manner and the structure is positioned within the central aperture or passage 29 defined by the rings. Suture spring device 22 can be inserted into the guide prior to or after positioning the guide in relation to the anatomical tissue. In either case, the suture spring device is ultimately positioned around the tubular structure T in an elastically deformed, expanded state and is then released from the guide by unscrewing the guide from the device as shown in FIG. 9 or, in other words, by rotating the guide in an opposite, counterclockwise direction, looking distally, while at the same time maintaining the suture spring device in a substantially stationary position in relation to the tubular anatomical structure by holding knob 34 to prevent rotation of the device. Slot 48 in the positioner facilitates release of the suture spring device from the guide by allowing the guide to slide past the knob as the guide is unscrewed. Once the guide is removed, rings 28 of the suture spring device are no longer radially and axially restrained by the guide and are thus free to move from their elastically deformed, expanded state toward the relaxed, contracted state as shown in FIG. 10 thereby compressing the walls of the tubular anatomical structure radially inward to occlude the lumen defined by the structure.

A modification of the guide for use with the suture spring device according to the present invention is shown in FIG. 11, wherein the modified guide 124 is similar to guide 24 but with a sharp, tissue penetrating tip 144 at the distal end. Use of guide 124 to position a suture spring device 122 around a tubular anatomical structure $T_1$ adhered to an adjacent tissue structure $T_2$ is illustrated in FIGS. 12 and 13. Sharp, distal tip 144 of the positioner is moved to penetrate into and through tissue $T_2$ near the line of adhesion as shown in FIG. 12 to position the tubular structure $T_1$ between the tip of the guide and an adjacent ring 138 proximally spaced from the tip, after which the guide is rotated clockwise, looking distally, to thread or coil all of the rings of the guide around the tubular structure as described above for suture spring device 120. After each complete revolution around the tubular structure, tip 144 will have moved axially a predetermined distance to penetrate into and through the adjacent tissue structure to establish a path through the tissue which is followed by the remaining rings as they coil around the tubular structure. When the rings of the guide containing the suture spring device are disposed around tubular structure $T_1$, the guide is removed from the tissue as described above to release the suture spring device so that the device will move toward the relaxed, contracted state as shown in FIG. 13 in order to apply a radially compressive load to the tubular anatomical structure disposed concentrically within rings 128 of the device.

A further modification of the suture spring device and guide according to the present invention is shown in FIG. 14 wherein the modified system 220 includes a suture spring device 222 similar to suture spring device 22 described above but without a knob and a tubular guide 224 similar to guide 24 described above but without a slot. The assembly further includes a pusher 252 having an elastic rod or finger slidable within the lumen 246 of the guide. In use, suture spring device 222 is inserted into guide 224 with or without use of pusher 252 and is held in a substantially stationary position around a tubular anatomical structure by the pusher while the guide is removed by sliding along the pusher in a proximal direction.

Another method of ligating anatomical tissue T according to the present invention is shown in FIGS. 15 and 16 and includes orienting a guide 24 substantially perpendicular to a longitudinal axis of the tissue and moving the guide laterally to position the tissue in the axial space between a pair of rings 38. Suture spring device 22 is held within the guide in an elastically deformed, axially expanded state so that, when the guide is removed from the suture spring device, rings 28 of the suture spring device are no longer axially restrained by the guide and are free to move from their elastically deformed, expanded state toward the relaxed, contracted state as shown in FIG. 16 thereby trapping that portion of the tissue disposed between the rings and applying an axially compressive force to ligate the tissue.

While a suture spring device has been shown threaded or coiled around a single anatomical structure in FIGS. 7–10, it will be appreciated that a single suture spring device can be threaded or coiled around two or more anatomical structures in an elastically deformed, expanded state and allowed to contract to ligate the structures in substantially the same manner as described above for a single anatomical structure. For example, in FIG. 17, a suture spring device 22 is shown ligating a tubular anatomical structure T which has been bent upon itself to form a loop or knuckle K; for example using a tissue grasping instrument as described in my aforementioned co-pending application Ser. No. 08/610,735, filed Mar. 5, 1996 and entitled "Suture Spring Device Applicator." The suture spring device is coiled around the base of the knuckle to occlude the lumen of the tubular anatomical structure at a pair of spaced locations simultaneously.

The suture spring device can also be used to close an opening in anatomical tissue, for example, as part of a hernia repair or after a polypectomy, by inverting edges of the tissue T adjacent the opening O, for example using the tissue grasping instrument referred to above, to form the tissue into a generally tubular shape as shown by broken lines in FIG. 18. Once inverted, the tissue may be approximated to close the opening by positioning the suture spring device 22 around the inverted tissue in a concentric manner as described above and then allowing the device to contract radially to approximate the tissue as shown in FIG. 19.

From the above, it will be appreciated that anatomical tissue can be ligated with a suture device of coiled configuration by positioning the suture device in relation to the tissue in an expanded state and causing the suture spring device to move toward a contracted state in order to apply a predetermined compressive force to the tissue. The force can be applied axially from opposite sides of the tissue by positioning the tissue in the axial space between rings of the suture device when the device is in an axially expanded state and causing the device to axially contract, or a radially compressive force can be applied by positioning the tissue concentrically within the longitudinal passage or aperture defined by rings of the suture device when the device is in a radially expanded state and causing the rings to move radially inward toward the contracted state. The suture device is preferably positioned around anatomical tissue using a guide having a configuration to hold the suture device in the expanded state. The guide can have a blunt, rounded tip as shown, a tissue penetrating tip, or the distal end of the suture device can be used as a tissue penetrating tip either alone or in combination with the distal end of the guide.

The suture device is preferably a suture spring device formed of an elastic body of coiled configuration, where by "elastic" is meant having an ability to recover an original shape or position after having been deformed and by "coiled" is meant defining a single coil or ring, a portion of a coil or ring or a series of connected coils or rings. Any number of rings or coils can be connected to make up a suture spring device according to the present invention. The rings can be circular, elliptical, polygonal or have any other curved or angular configuration in cross-section and, when a device has more than one ring, adjacent rings can be of the same size and shape or of different size and shape depending on the desired tissue engaging shape of the device. For example, the rings can form conical, bi-conical, cylindrical, spherical or pyramidal surfaces when viewed in elevation from the side. The body of the suture spring device can be solid or hollow and can have any configuration in cross-section including, but not limited to, circular, rectangular, elliptical and polygonal configurations. If the body of the suture spring device is hollow, the guide can be disposed within the body to maintain the suture spring device in the elastically deformed, expanded state. In addition, the exterior surface of the body of the suture spring device can be smooth as shown or provided with means for locking the suture device in tissue to prevent forward and/or rearward movement, such as the locking means shown and described in U.S. Pat. No. 5,053,047 to Yoon, the contents of which are incorporated herein by reference. The suture spring device can be made of any suitable, medical grade material but is preferably formed of an elastic or resilient material, that is, a material able to recover its original position or shape after having been deformed. Furthermore, the spring material can be bioabsorbable or non-bioabsorbable depending on the length of time the tissue is required to be held together. Generally, suitable bioabsorbable materials include thermoplastic polymers such as absorbable polymers and copolymers of poly-dioxane, lactide, glycolide and the like. Polyglycolic acid is disclosed in U.S. Pat. Nos. 3,463,158; 3,739, 773; and 3,772,420. Suitable polylactic acids are disclosed in U.S. Pat. No. 3,636,956. Examples of absorbable polyesters are shown in U.S. Pat. Nos. 3,225,766 and 3,883,901. Absorbable cellulose glycolic acid ethers are shown in U.S. Pat. No. 2,764,159. Examples of suitable esters of alpha-cyanoacrylic acid are found in U.S. Pat. Nos. 3,527,841; 3,564,078 and 3,759,264. Further details of the suture spring device are set forth in my above-referenced co-pending application Ser. No. 08/610,951, filed Mar. 5, 1996, entitled "Suture Spring Device," and several embodiments of suitable suture devices are disclosed therein.

Once the suture spring device is positioned in or with respect to the tissue, the return of the suture spring device toward the rest position can be enhanced, dependent upon the material from which the suture spring device is constructed, by temperature change and/or by the application of electricity, light or other energy to alter the characteristics of the material.

When the suture spring device is provided with a knob or handle, it can be formed separately from the body of the device and connected thereto by any suitable method, such as by welding, or the knob can be formed integrally with the body as a one-piece unit. The knob can have any shape to protrude from the guide including, but not limited to, the spherical shape shown as well as cylindrical, rectangular, elliptical and conical shapes. Furthermore, the knob can be formed by the body of the device itself by turning the proximal end of the body inwardly or outwardly relative to a longitudinal axis of the device. It will also be appreciated that the handle or knob can be placed anywhere on the spring although it is preferred that the knob be placed near the proximal end of the device so as not to interfere with the penetration of the device through anatomical tissue.

The guide can be made of any suitable medically acceptable material, such as stainless steel, so long as it is configured to have a stiffness suitable for maintaining the suture spring device in the expanded state in anatomical tissue. The guide is preferably of coiled configuration as shown but can also be of straight configuration if desired. Depending upon the manner in which the suture spring device is moved relative to the guide, the guide can be formed with or without a slot. When formed with a slot, the slot will preferably extend from a proximal end of the guide to a distal end of the guide and will communicate between an exterior surface of the guide and an interior lumen. The slot can have tapered or V-shaped sides to accommodate a ball-shaped handle as shown, or the sides of the slot can be straight. Furthermore, although the slot is shown on the outer, convex side of the guide, it can be formed on the inner, concave side or anywhere inbetween or the slot can be made to spiral around the coiled body of the guide. Further details of the guide are set forth in my above-referenced co-pending application Ser. No. 08/610,951, filed Mar. 5, 1996, entitled "Suture Spring Device," and several embodiments of suitable guides are disclosed therein.

Any type of force can be used to move the suture spring device relative to the guide including, but not limited to, mechanical forces provided by springs, magnetic forces and/or hydraulic or pneumatic forces. The suture spring device and guide can be held and manipulated using standard needle-holding instruments and forceps, can be grasped directly by hand, or can be used with an instrument specifically designed to apply suture spring devices according to the present invention. For example, the suture spring device could be applied using any of the applicators shown and described in my aforementioned co-pending patent application Ser. No. 08/610,735, filed Mar. 5, 1996, entitled "Suture Spring Device Applicator."

The features of the various embodiments described above can be combined in any manner desired dependant upon the operational requirements of the procedure to be performed and the complexity of the particular design.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of ligating anatomical tissue using a suture spring device of coiled configuration having a plurality of connected rings, said method comprising the steps of expanding the suture spring device from a relaxed, unexpanded state to an elastically deformed, expanded state;

holding the suture spring device in the expanded state using a guide;

positioning the anatomical tissue in an axial space between rings of the suture spring device when the device is held by the guide in the elastically deformed, expanded state; and causing the suture spring device to contract from the elastically deformed, expanded state toward the relaxed, unexpanded state to ligate the anatomical tissue.

2. A method of ligating anatomical tissue as recited in claim 1 wherein said positioning step includes holding the suture spring device in the elastically deformed, expanded state within a hollow tubular guide of coiled configuration.

3. A method of ligating anatomical tissue as recited in claim 2 wherein said causing step includes removing the guide from the suture spring device to allow the suture spring device to contract resiliently from the elastically deformed, expanded state toward the relaxed, unexpanded state to ligate the anatomical tissue.

4. A method of ligating anatomical tissue as recited in claim 3 wherein said causing step further includes maintaining the suture spring device substantially stationary as the guide is removed.

5. A method of ligating anatomical tissue as recited in claim 4 wherein said maintaining step includes holding a knob extending laterally outward from the suture spring device through a slot in the guide and said removing step includes sliding the guide past the knob in a proximal direction.

6. A method of ligating anatomical tissue as recited in claim 4 wherein said maintaining step includes advancing a pusher through the guide to abut a proximal end of the suture spring device and said removing step includes sliding the guide over the pusher in a proximal direction.

7. A method of ligating anatomical tissue using a suture spring device of coiled configuration having a plurality of connected rings, said method comprising the steps of expanding the suture spring device from a relaxed, unexpanded state to an elastically deformed, expanded state;

positioning the anatomical tissue in an axial space between rings of the suture spring device when the device is in the elastically deformed, expanded state; and causing the suture spring device to contract from the elastically deformed, expanded state toward the relaxed, unexpanded state to ligate the anatomical tissue;

wherein said expanding step includes increasing a radius of curvature of the rings of the suture spring device and further comprising the step of repositioning the anatomical tissue relative to the suture spring device when the device is in the elastically deformed, expanded state so that, when the suture spring is caused to move from the expanded state to the relaxed, unexpanded state, the rings will contract radially to ligate the anatomical tissue disposed therein.

8. A method of ligating anatomical tissue as recited in claim 7 wherein said positioning step includes positioning the anatomical tissue between a distal tip of the suture spring device and a ring axially spaced from the tip when the suture spring device is in the elastically deformed, expanded state, and said repositioning step includes rotating the suture spring device to cause the tip of the device and the rings to coil around the anatomical tissue.

9. A method of ligating anatomical tissue as recited in claim 7 wherein said positioning step includes inverting anatomical tissue adjacent an opening in the tissue and placing the elastically deformed, expanded suture spring device around the inverted anatomical tissue so that, when the suture spring device is allowed to contract, the inverted tissue will be drawn together to close the opening.

10. A method of ligating anatomical tissue as recited in claim 8 wherein said positioning step includes passing the suture spring device through an anatomical structure adjacent the anatomical tissue.

11. A method of ligating anatomical tissue as recited in claim 10 wherein said passing step includes penetrating the adjacent anatomical structure with a hollow, tubular guide of coiled configuration having a sharp, tissue penetrating tip, and using the guide to pass the suture spring device through the adjacent anatomical structure.

12. A method of ligating anatomical tissue as recited in claim 1 wherein said expanding step includes increasing the axial spacing between rings so that, when the suture spring device is caused to contract, the rings will contract axially to ligate the anatomical tissue disposed therebetween.

13. A suture spring device and guide for ligating anatomical tissue, said suture spring device comprising an elastic body of coiled configuration having a relaxed, contracted state and an elastically deformed, expanded state; and said guide comprising an elongate tubular body of coiled configuration having a blunt distal tip, said guide having a configuration to hold said suture spring device therein in said elastically deformed, expanded state and to be removable from said suture spring device to permit said device to move resiliently from said expanded state toward said contracted state to ligate anatomical tissue engaged by said coiled body of said device.

14. A suture spring device and guide as recited in claim 13 wherein said hollow tubular body of said guide is formed with a slot extending between proximal and distal ends of said guide and communicating between interior and exterior surfaces of said hollow tubular body.

15. A suture spring device and guide as recited in claim 14 wherein said slot has a width to prevent said suture spring device from passing therethrough when said suture spring device is disposed within said guide.

16. A suture spring device and guide as recited in claim 14 wherein said suture spring device includes a knob that extends laterally through said slot when said suture spring device is disposed within said guide.

17. A suture spring device and guide as recited in claim 16 wherein said knob includes a ball disposed adjacent said proximal end of said suture spring device.

18. A suture spring device and guide as recited in claim 16 wherein said hollow, tubular body of said guide has a predetermined radius of curvature and said slot is formed on a convex side of said hollow, tubular body.

19. A suture spring device and guide as recited in claim 18 wherein said predetermined radius of curvature is greater than a radius of curvature of said suture spring device in said relaxed, contracted state.

20. A suture spring device and guide as recited in claim 18 wherein said coiled tubular body of said guide includes a plurality of connected rings having a predetermined axial spacing therebetween and said suture spring device includes a plurality of connected rings having an axial spacing therebetween in said relaxed, contracted state which is less than said predetermined axial spacing of said guide rings.

21. A suture spring device and guide as recited in claim 18 wherein said coiled tubular body of said guide includes a plurality of connected rings having a predetermined radius of curvature and a predetermined axial spacing therebetween and said suture spring device includes a plurality of connected rings having a radius of curvature and an axial spacing therebetween in said relaxed, contracted state which is less than said predetermined radius of curvature and said predetermined axial spacing of said guide rings.

22. A method of ligating anatomical tissue using a suture device of coiled configuration having a plurality of connected rings, said method comprising the steps of holding the suture device in an expanded state using a guide;

positioning the anatomical tissue in an axial space between rings of the suture device when the device is held by the guide in the expanded state; and causing the suture device to move from the expanded state toward the contracted state to ligate the anatomical tissue.

23. A method of ligating anatomical tissue using a suture device of coiled configuration having a plurality of connected rings, said method comprising the steps of holding the suture device in an expanded state;

positioning the anatomical tissue in an axial space between rings of the suture device when the device is in the expanded state;

repositioning the anatomical tissue relative to the suture device by positioning the anatomical tissue between a distal tip of the suture device and a ring axially spaced from the tip and rotating the suture device to cause the tip of the device and the rings to coil around the anatomical tissue; and causing the suture device to move from the expanded state toward the contracted state to ligate the anatomical tissue, wherein said causing step includes causing the suture device to contract radially inward to ligate the anatomical tissue disposed concentrically within the rings of the device.

24. A method of ligating anatomical tissue as recited in claim 22 wherein said causing step includes causing the suture device to contract axially to ligate the anatomical tissue disposed between rings of the suture device.

25. A method of ligating anatomical tissue as recited in claim 22 wherein said holding step includes holding the suture device in the expanded state within a guide of coiled configuration having a plurality of connected rings, and said positioning step includes positioning the anatomical tissue an axial space between rings of the guide.

* * * * *